(12) United States Patent
Hu et al.

(10) Patent No.: US 11,992,563 B2
(45) Date of Patent: May 28, 2024

(54) COMPOSITE MATERIAL FOR RAPID BLOOD CLOTTING AND PREPARATION METHOD THEREOF

(71) Applicant: Guangdong Ocean University, Zhanjiang (CN)

(72) Inventors: Zhang Hu, Zhanjiang (CN); Lefan Li, Zhanjiang (CN); Yu Cheng, Hangzhou (CN); Mingneng Liao, Zhanjiang (CN)

(73) Assignee: Guangdong Ocean University, Zhanjiang (CN)

( * ) Notice: Subject to any disclaimer, the term of this patent is extended or adjusted under 35 U.S.C. 154(b) by 0 days.

(21) Appl. No.: 18/341,748

(22) Filed: Jun. 26, 2023

(65) Prior Publication Data
US 2023/0338607 A1   Oct. 26, 2023

Related U.S. Application Data

(63) Continuation of application No. PCT/CN2022/070418, filed on Jan. 6, 2022.

(30) Foreign Application Priority Data

Oct. 22, 2021   (CN) .......................... 202111231246.6

(51) Int. Cl.
  *A61L 15/28*   (2006.01)
  *A61L 15/18*   (2006.01)

(52) U.S. Cl.
  CPC .............. *A61L 15/28* (2013.01); *A61L 15/18* (2013.01); *A61L 2300/418* (2013.01); *A61L 2400/04* (2013.01)

(58) Field of Classification Search
  None
  See application file for complete search history.

(56) References Cited

PUBLICATIONS

Nakamura et al. (Controlled synthesis of a chitosan-based graft copolymer having polysarcosine side chains using the NCA method with a carboxylic acid additive), Macromolecular Rapid Communications, 27, 1725-1732 (Year: 2006).*
Tarighi et al. (A review on common chemical hemostatic agents in dentistry), Dental Research Journal, vol. 11, Issue 4, 423-428, July (Year: 2014).*
Shou et al. (Thermoresponsive chitosan/DOPA-based hydrogel as an injectable therapy approach for tissue-adhesion and hemostasis), American Chemical Society biomaterial, 6, 3619-3629 (Year: 2020).*
Li et al. (Gel thermo-gelation behavior study of chitosan-inorganic phosphate solution), European Journal of Pharmaceutics and Biopharmaceutics, 75, 388-392 (Year: 2010).*

(Continued)

*Primary Examiner* — Isis A Ghali (57) ABSTRACT

A composite material for rapid blood clotting and its preparation method are provided. The composite material includes the following raw materials in parts by weight: 8~20 parts of chitosan, 7~14 parts of salicylaldehyde, 8~16 parts of 2-aminoisonicotinic acid, 1.5~3.5 parts of ferrous sulfate, 3~5 parts of dopa, and 10~15 parts of disodium hydrogen phosphate. The composite material for rapid blood clotting has good stability, high biological safety, significant effects on blood clotting, simple process, and easy industrial production.

4 Claims, 3 Drawing Sheets

(56) References Cited

PUBLICATIONS

Wu et al. (The efficient hemostatic effect of Antarctic krill chitosan is related to its hydration property), Carbohydrate Polymers, 132, 295-303. (Year: 2015).*
Wang et al. (Chitosan: Structural modification, biological activity and application), International Journal of Biological Macromolecules, 164, 4532-4546 (Year: 2020).*
Jing Guan et al, "preparation and blood coagulation property of ortho hydroxytoluene chitosan", "Material Science Forum", Mar. 3, 2017, vol. 893, pp. 62-68, 2017 Trans Tech Publications, Switzerland.

* cited by examiner

COMPOSITE MATERIAL FOR RAPID BLOOD CLOTTING AND PREPARATION METHOD THEREOF

TECHNICAL FIELD

The disclosure relates to the technical field of agriculture, and particularly to a composite material for rapid blood clotting and a preparation method thereof.

BACKGROUND

According to statistics, uncontrolled hemorrhage is the main cause of death, and hemorrhagic shock death accounts for 30% to 45% of traumatic injury deaths every year. Therefore, the development of efficient hemostatic materials is the key to rapid hemostasis and reduction of mortality caused by hemorrhage. Although hemostatic materials such as glutaraldehyde-crosslinked albumin and fibrin-based bandages have good hemostatic effects, it is usually difficult for traditional hemostatic agents to control this type of hemorrhage because of the lack of coagulation factors or dysfunction in patients with coagulation diseases, which increases the risk of death due to massive hemorrhage. Therefore, controlling hemostasis of hemorrhage with coagulopathy remains a great challenge. A Chinese patent with publication number of CN104114198A discloses a hemostatic wound dressing including a non-colloidal porous dressing material and multiple fibrinogen-binding peptides immobilized to the non-colloidal porous dressing material. The dressing can accelerate hemostasis, but has no effect on hemostasis caused by lack of coagulation factors or dysfunction in the patients with coagulation diseases.

Among the commercially available hemostatic materials, QuikClot® zeolite hemostatic powder is used for emergency treatment of severe bleeding trauma, but it will release a large amount of heat during use, resulting in local high temperature and re-injury of wound tissue. Powder hemostatic materials can easily remain in the lumen of vessels, blocking the flow of peripheral arteries and forming thrombi. For example, WoundStat™ hemostatic has the risk of entering the blood circulation system and causing peripheral thrombosis. How to prepare a blood clotting material with stable properties and high biological safety has become a technical problem to be solved by technicians in the field.

SUMMARY

A purpose of the disclosure is to provide a composite material for rapid blood clotting and a preparation method thereof to solve the problems in the prior art. The composite material with a significant effect on blood clotting is prepared by taking chitosan, salicylaldehyde, 2-amino isonicotinic acid, ferrous sulfate, dopa and disodium hydrogen phosphate as raw materials. The composite material has high stability and biological safety, and the preparation of the composite material is simple and easy for industrial production.

To achieve the above purpose, the disclosure provides following technical solutions.

According to one of the technical solutions of the disclosure, the composite material for rapid blood clotting includes following raw materials in parts by mass: 8~20 parts of chitosan, 7~14 parts of salicylaldehyde, 8~16 parts of 2-aminoisonicotinic acid, 1.5~3.5 parts of ferrous sulfate, 3~5 parts of dopa, and 10~15 parts of disodium hydrogen phosphate.

In an embodiment, the composite material includes the following raw materials in parts by mass: 14 parts of the chitosan, 10 parts of the salicylaldehyde, 12 parts of the 2-aminoisonicotinic acid, 2.5 parts of the ferrous sulfate, 4 parts of the dopa, and 13 parts of the disodium hydrogen phosphate.

Chitosan is a deacetylated product of chitin mainly extracted from the shells of marine crustaceans such as shrimps and crabs. Chitosan is widely used in the manufacture of artificial skin, surgical sutures, drug carriers and so on due to its non-toxicity, non-irritation, non-immunogenicity, non-pyrogenic reaction, non-hemolysis, biodegradation and good biocompatibility, and has attracted more and more attention in the field of hemostatic dressings. The blood clotting effect of chitosan is affected by multiple factors, such as structural unit, molecular mass, degree of deacetylation, cationic characteristics and so on.

Dopa is an amino acid organic compound extracted or synthesized from *quinoa* beans, which is an important component of the mucus secreted by marine mussels and other organisms. Dopa has strong adhesion, not only on the surface of inorganic materials, but also on the surface of organic materials. Strong adhesion of adhesive proteins secreted by the byssus of marine mussels in the water is particularly noticeable, and this excellent performance is incomparable with other adhesives at present. The strong adhesion of secretions of marine mussels exhibited in a wet environment is closely related to catechol structure.

The ferrous ion in ferrous sulfate is an important component of hemoglobin. Hemoglobin is a functional unit of erythrocytes, and erythrocytes are the carriers of hemoglobin. Hemoglobin is a tetramer composed of four subunits, each of the subunits has a pigment prosthetic group (i.e., heme). Heme is an iron-containing porphyrin compound, in which ferrous ions can reversibly combine with oxygen and participate in the transmission of oxygen in organisms.

In an embodiment, the molecular mass of the chitosan is 50~300 kilodaltons (KDa), and the degree of deacetylation of the chitosan (The degree of deacetylation represents a ratio of the number of deacetylated glucosamine units to the total number of glucosamine units) is 80~95%.

In an embodiment, the molecular mass of the chitosan is 100 KDa, and the degree of deacetylation of the chitosan is 90%.

If the molecular mass and the degree of deacetylation of the chitosan are too low, the blood clotting effect of the prepared composite material is not significant; if the molecular mass and the degree of deacetylation of the chitosan are too high, the difficulty of preparing the composite material is increased, the cost is greatly increased, and industrial production of the composite material is not easy to be realized.

According to one of the technical solutions of the disclosure, the composite material is prepared by the following steps:

step 1: adding an ethanol solution mixed with 2-amino isonicotinic acid and coupling agents into a chitosan solution to obtain a first mixture, and stirring the first mixture for reacting to obtain chitosan-amino isonicotinic acid graft; and the coupling agents including 1-ethyl-3-(3-dimethylaminopropyl) carbodiimide hydrochloride and N-hydroxysuccinimide; and step 2: dissolving the chitosan-amino isonicotinic acid graft prepared in the step 1 to obtain a chitosan-amino isonicotinic acid graft solution, adjusting a potential of hydrogen (pH) value of the chitosan-amino isonicotinic acid graft solution to 5.0~7.0, adding the salicylaldehyde and stirring for a predetermined time, sequentially adding the ferrous sulfate, the dopa and the disodium hydrogen phosphate for evenly mixing to obtain a second mixture; and standing the second mixture in a dark place to obtain the composite material.

When the ferrous sulfate is added first, it is beneficial to the formation of coordination compounds, resulting in a significant blood clotting effect; if ferrous sulfate is added later, the dopa or disodium hydrogen phosphate added first is easy to produce hydrogen bonding or electrostatic interaction with chitosan-based ligand groups, which hinders the coordination of ferrous ions, resulting in the reduction of the adsorption and aggregation ability of the composite material on erythrocytes and the weakening of the blood clotting effect.

In an embodiment, a solvent in the chitosan solution is an acetic acid aqueous solution, and a mass fraction of chitosan in the chitosan solution is 2~5%.

In an embodiment, a mass fraction of chitosan in the chitosan solution is 3%.

If the mass concentration of the chitosan solution is too low, the difficulty of a subsequent process to prepare the composite material is increased, and the blood clotting effect of the composite material is not ideal; if the mass concentration of the chitosan solution is too high, the solution system is too viscous, so that the reaction is uneven, and the blood clotting effect of the composite material is poor.

In an embodiment, a mass fraction of acetic acid in the acetic acid aqueous solution is 2%.

In an embodiment, a molar ratio of the 1-ethyl-3-(3-dimethylaminopropyl) carbodiimide hydrochloride to the N-hydroxysuccinimide is 5:1.

In an embodiment, a volume of the absolute ethanol is 10~30% of a volume of the acetic acid aqueous solution.

In an embodiment, the volume of the absolute ethanol is 20% of the volume of the acetic acid aqueous solution.

If the volume of absolute ethanol is too small, the solute concentration is too high, and then the absolute ethanol is added into the chitosan solution and makes the reaction be uneven, and the blood clotting effect of the composite material is poor; if the volume of the absolute ethanol is too large, then the absolute ethanol is added into the chitosan solution, so that the chitosan will be directly separated out, and the finally prepared composite material has no significant blood clotting effect.

In an embodiment, a molar ratio of the 2-aminoisonicotinic acid to the 1-ethyl-3-(3-dimethylaminopropyl) carbodiimide hydrochloride is 2:3 in the ethanol solution of the step 1.

In an embodiment, a duration of the stirring in the step 1 is 6~8 hours (h). In the step 2, the pH value is 5.5, a reagent used for adjusting the pH value is 0.1 moles per liter (mol/L) HCl solution, and the predetermined time in the step 2 is 4~6 h.

If the pH value is too small (pH<5.0), the acidity is too strong, making it difficult to form Schiff base by condensation of salicylaldehyde and amino groups; If the pH value is too high (pH>7.0), ferrous ions are unstable in the system and are prone to precipitation. Therefore, the pH value is preferably 5.0~7.0, more preferably 5.5.

The disclosure has following technical effects:
(1) The composite material of the disclosure has a rapid blood clotting effect independent of normal blood clotting methods, and is particularly suitable for hemostasis of hemorrhage with coagulopathy.
(2) The disclosure first uses the coupling agents composed of 1-ethyl-3-(3-dimethylaminopropyl) carbodiimide hydrochloride (EDC·HCl) and N-hydroxysuccinimide (NHS) to introduce 2-aminoisonicotinic acid onto a molecular chain of chitosan through an acylation reaction. Then, Schiff base is formed by condensation of salicylaldehyde and amino groups on 2-aminoisonicotinic acid to form a ligand for ferrous ions. After the coupling agents react with the ferrous sulfate, a chitosan based-$Fe^{2+}$ complex is formed. On the one hand, the complex is cross-coordinated with the hemoglobin in erythrocytes by $Fe^{2+}$ (i.e., ferrous ion), promoting erythrocyte aggregation; on the other hand, the protonated amino groups (with positive charge) in chitosan interacts with surfaces (with negative charge) of erythrocytes to perform synergistic adsorption and aggregation effects on the erythrocytes. In-vitro blood clotting tests prove that the composite material having the chitosan based-$Fe^{2+}$ complex promotes the adsorption and aggregation of the erythrocytes in the blood, resulting in a significant blood clotting effect.
(3) The disclosure uses the inner salt characteristic of amino acids in a dopa structure to realize the formation of a charge transfer compound, which is beneficial to the formation of intermolecular hydrogen bonds in the composite material and enhances the stability of the composite material. Meanwhile, by using the strong reducibility of a catechol structure in the dopa structure can effectively protect $Fe^{2+}$ in the composite material from being oxidized, and $Fe^{2+}$ in the composite material have strong stability. In addition, the catechol structure in the dopa structure have similar characteristics with adhesive proteins of mussels, so that the composite material has strong adhesiveness after absorbing liquids to form a hydrogel and can effectively blocks a bleeding opening, and is particularly suitable for emergency treatment of massive hemorrhage caused by deep and narrow bleeding openings.
(4) Disodium hydrogen phosphate of the composite material interact with protonated amino groups (cation) of chitosan to generate electrostatic and hydrogen bond effects by using the characteristics of hydrogen phosphate anions and hydroxyl in the structure of the disodium hydrogen phosphate, so that the composite material has a stable porous structure, can rapidly absorb liquids and swell to form a hydrogel, has a certain volume, and is not easy to enter blood to cause thrombus. In addition, the small molecular structure of the disodium hydrogen phosphate promotes the structural stability of the composite material, does not hinder the coordination of $Fe^{2+}$, and is beneficial to blood clotting.
(5) The composite material prepared by the disclosure has low hemolysis rate and high biological safety; The preparation method of the composite material is simple and easy to realize industrial production.

BRIEF DESCRIPTION OF DRAWINGS

In order to more clearly describe embodiments of the disclosure or the technical solutions in the prior art, attached drawings required in the embodiments will be briefly described below. Apparently, the attached drawings in the following description are only some of the embodiments of the disclosure. For those of ordinary skilled in the art, other attached drawings can also be obtained from these attached drawings.

DETAILED DESCRIPTION OF EMBODIMENTS

Various exemplary embodiments of the disclosure will now be described in detail. The detailed description should not be considered to be a limitation of the disclosure, but rather should be understood as a more detailed description of certain aspects, features, and embodiments of the disclosure.

It is to be understood that terms used in the disclosure are only for a purpose of describing specific embodiments and are not intended to limit the disclosure. In addition, with respect to any numerical range in the disclosure, it should be understood that each intermediate value between upper and lower limits of the numerical range is specifically disclosed as well. Every intermediate values within any stated range and every lesser range between the intermediate values within any stated range should also be included in the disclosure. Upper and lower limits of these lesser ranges may be independently included or excluded in the stated range.

Unless otherwise indicated, all technical and scientific terms used in the disclosures have the same meaning as commonly understood by those ordinary skilled in the art. Although only some methods and materials have been described herein, any methods and materials similar or equivalent to those described herein can be used in the embodiments or tests of the disclosure. All documents mentioned in this specification are incorporated by reference for the purpose of disclosing and describing methods and/or materials associated with documents. In the event of a conflict with any incorporated documents, the contents of this specification shall prevail.

It is apparent to those skilled in the art that various modifications and improvements can be made in specific embodiments described herein without departing from the scope or spirit of the disclosure. Other embodiments are apparent to those skilled in the art from this specification of the disclosure. The specification and embodiments of the disclosure are exemplary only.

Terms "include", "comprise", "have", "contain", and so on used in the disclosure are all open-ended terms, meaning that the terms refer to include but not limited to.

Embodiment 1

A preparation method of a composite material for rapid blood clotting includes following steps.

Step (1): mixing 4526 g of an acetic acid aqueous solution (a mass fraction of acetic acid in the acetic acid aqueous solution is 2%) with 140 g of chitosan (a molecular mass of the chitosan is 100 KDa and a degree of deacetylation of the chitosan is 90%) for dissolving the chitosan, thereby to obtain a chitosan solution.

Step (2): dissolving 120 g (0.8688 mol) of 2-aminoisonicotinic acid in absolute ethanol (a volume of the absolute ethanol is 20% of a volume of the acetic acid aqueous solution in the step (1)), adding coupling agents (the coupling agents include 1.3032 mol of EDC·HCl and 0.2606 mol of NHS), and stirring at a room temperature (about 25° C.) for 3 hours (h) to obtain an ethanol solution mixed with 2-aminoisonicotinic acid and coupling agents.

Step (3): adding the ethanol solution mixed with 2-aminoisonicotinic acid and coupling agents prepared in the step (2) to the chitosan solution prepared in step (1), thereby to obtain a first mixture; stirring at the room temperature for 8 h, dialyzing with distilled water, freezing and drying to obtain chitosan-amino isonicotinic acid graft.

Figure 1:
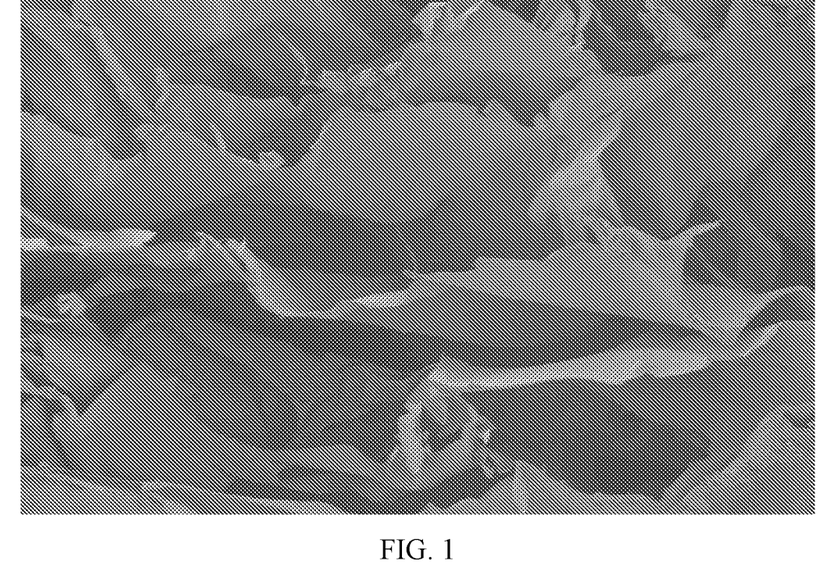
FIG. 1 illustrates a scanning electron micrograph of a composite material for rapid blood clotting prepared in embodiment 1 of the disclosure.

Step (4): dissolving the chitosan-amino isonicotinic acid graft prepared in the step (3) in 4526 g of the acetic acid aqueous solution (the mass fraction of acetic acid in the acetic acid aqueous solution is 2%) to obtain a chitosan-amino isonicotinic acid graft solution, adjusting a pH value of the chitosan-amino isonicotinic acid graft solution to 5.5 by 0.1 mol/L of HCl solution, then adding 100 g of salicylaldehyde under a stirring condition, after stirring for 5 h, adding 25 g of ferrous sulfate, 40 g of dopa and 130 g of disodium hydrogen phosphate in turn for evenly mixing to obtain a second mixture at the room temperature, standing the second mixture in a dark place for 12 h, and freezing and drying to obtain the composite material for rapid blood clotting. A scanning electron micrograph of the composite material is shown in FIG. 1.

Embodiment 2

A preparation method of a composite material for rapid blood clotting includes following steps.

Step (1): mixing 3840 g of an acetic acid aqueous solution (a mass fraction of acetic acid in the acetic acid aqueous solution is 2%) with 160 g of chitosan (a molecular mass of the chitosan is 100 KDa and a degree of deacetylation of the chitosan is 90%) for dissolving the chitosan, thereby to obtain a chitosan solution.

Step (2): dissolving 100 g (0.724 mol) of 2-aminoisonicotinic acid in absolute ethanol (a volume of the absolute ethanol is 20% of a volume of the acetic acid aqueous solution in the step (1)), adding coupling agents (the coupling agents include 1.086 mol of EDC·HCl and 0.2172 mol of NHS), and stirring at a room temperature (about 25° C.) for 3 h to obtain an ethanol solution mixed with 2-aminoisonicotinic acid and coupling agents.

Step (3): adding the ethanol solution mixed with 2-aminoisonicotinic acid and coupling agents prepared in the step (2) to the chitosan solution prepared in step (1), thereby to obtain a first mixture; stirring at the room temperature for 7 h, dialyzing with distilled water, freezing and drying to obtain chitosan-amino isonicotinic acid graft.

Step (4): dissolving the chitosan-amino isonicotinic acid graft prepared in the step (3) in 3840 g of the acetic acid aqueous solution (the mass fraction of acetic acid in the acetic acid aqueous solution is 2%) to obtain a chitosan-amino isonicotinic acid graft solution, adjusting a pH value of the chitosan-amino isonicotinic acid graft solution to 6.0 by 0.1 mol/L of HCl solution, then adding 120 g of salicylaldehyde under a stirring condition, after stirring for 6 h, adding 20 g of ferrous sulfate, 35 g of dopa and 110 g of disodium hydrogen phosphate in turn for evenly mixing to obtain a second mixture at the room temperature, standing the second mixture in a dark place for 12 h, and freezing and drying to obtain the composite material for rapid blood clotting.

Embodiment 3

A preparation method of a composite material for rapid blood clotting includes following steps.

Step (1): mixing 3920 g of an acetic acid aqueous solution (a mass fraction of acetic acid in the acetic acid aqueous solution is 2%) with 80 g of chitosan (a molecular mass of the chitosan is 100 KDa and a degree of deacetylation of the chitosan is 90%) for dissolving the chitosan, thereby to obtain a chitosan solution.

Step (2): dissolving 80 g (0.5792 mol) of 2-aminoisonicotinic acid in absolute ethanol (a volume of the absolute ethanol is 30% of a volume of the acetic acid aqueous solution in the step (1)), adding coupling agents (the coupling agents include 0.8688 mol of EDC·HCl and 0.1738 mol of NHS), and stirring at a room temperature (about 25° C.) for 3 hours to obtain an ethanol solution mixed with 2-aminoisonicotinic acid and coupling agents.

Step (3): adding the ethanol solution mixed with 2-aminoisonicotinic acid and coupling agents prepared in the step (2) to the chitosan solution prepared in step (1), thereby to obtain a first mixture; stirring at the room temperature for 6 hours, dialyzing with distilled water, freezing and drying to obtain chitosan-amino isonicotinic acid graft.

Step (4): dissolving the chitosan-amino isonicotinic acid graft prepared in the step (3) in 3920 g of the acetic acid aqueous solution (the mass fraction of acetic acid in the acetic acid aqueous solution is 2%) to obtain a chitosan-amino isonicotinic acid graft solution, adjusting a pH value of the chitosan-amino isonicotinic acid graft solution to 7.0 by 0.1 mol/L of HCl solution, then adding 70 g of salicylaldehyde under a stirring condition, after stirring for 4 hours, adding 15 g of ferrous sulfate, 30 g of dopa and 100 g of disodium hydrogen phosphate in turn for evenly mixing to obtain a second mixture at the room temperature, standing the second mixture in a dark place for 12 h, and freezing and drying to obtain the composite material for rapid blood clotting.

Embodiment 4

A preparation method of a composite material for rapid blood clotting includes following steps.

Step (1): mixing 3800 g of an acetic acid aqueous solution (a mass fraction of acetic acid in the acetic acid aqueous solution is 2%) with 200 g of chitosan (a molecular mass of the chitosan is 100 KDa and a degree of deacetylation of the chitosan is 90%) for dissolving the chitosan, thereby to obtain a chitosan solution.

Step (2): dissolving 160 g (1.1584 mol) of 2-aminoisonicotinic acid in absolute ethanol (a volume of the absolute ethanol is 10% of a volume of the acetic acid aqueous solution in the step (1)), adding coupling agents (the coupling agents include 1.7376 mol of EDC·HCl and 0.3475 mol of NHS), and stirring at a room temperature (about 25° C.) for 3 hours to obtain an ethanol solution mixed with 2-aminoisonicotinic acid and coupling agents.

Step (3): adding the ethanol solution mixed with 2-aminoisonicotinic acid and coupling agents prepared in the step (2) to the chitosan solution prepared in step (1), thereby to obtain a first mixture; stirring at the room temperature for 8 hours, dialyzing with distilled water, freezing and drying to obtain chitosan-amino isonicotinic acid graft.

Step (4): dissolving the chitosan-amino isonicotinic acid graft prepared in the step (3) in 3920 g of the acetic acid aqueous solution (the mass fraction of acetic acid in the acetic acid aqueous solution is 2%) to obtain a chitosan-amino isonicotinic acid graft solution, adjusting a pH value of the chitosan-amino isonicotinic acid graft solution to 5.0 by 0.1 mol/L of HCl solution, then adding 140 g of salicylaldehyde under a stirring condition, after stirring for 5 hours, adding 35 g of ferrous sulfate, 50 g of dopa and 150 g of disodium hydrogen phosphate in turn for evenly mixing to obtain a second mixture at the room temperature, standing the second mixture in a dark place for 12 hours, and freezing and drying to obtain the composite material for rapid blood clotting.

Contrastive Example 1

Operations of the contrastive example 1 are the same as embodiment 1 basically, the difference is that in step (2) of the contrastive example 1, 2-aminoisonicotinic acid is replaced with 3-aminobenzoic acid.

Contrastive Example 2

Operations of the contrastive example 2 are the same as embodiment 1 basically, the difference is that in step (4) of the contrastive example 2, the disodium hydrogen phosphate is replaced with β-Sodium glycerophosphate.

Contrastive Example 3

Operations of the contrastive example 3 are the same as embodiment 1 basically, the difference is that in step (4) of the contrastive example 2, the ferrous sulfate is not added.

Contrastive Example 4

140 g of chitosan, 120 g of 2-aminoisonicotinic acid, 100 g of salicylaldehyde, 25 g of ferrous sulfate, 40 g of dopa, and 130 g of disodium hydrogen phosphate are taken as raw materials to be added into 4526 g of acetic acid aqueous solution (the mass fraction of acetic acid in the acetic acid aqueous solution is 2%), operations of suspending evenly, freezing and drying are performed next, and the composite material is obtained.

Effective Test 1

In-Vitro Blood Clotting Test:
Blood clotting index (BCI) is used to evaluate the in-vitro blood clotting performance of the composite material of the disclosure. Blood is taken from the ear vein of New Zealand rabbits and put into vacuum blood collection tubes (the tubes contains sodium citrate anticoagulant, a ratio of 3.8% sodium citrate: blood is 1:9) for later use. 0.1 g of the composite material prepared in each of embodiments 1~4 and contrastive examples 1~4, and 0.1 g of a positive contrast (Yunnan Baiyao) are respectively spread at a bottom of a 50 mL centrifuge tube. Each the centrifuge tube is taken as a test sample and is put into a constant temperature shaker at a temperature of 37° C. to be incubated for 5 min, then 20 microliters (μL) of fresh anticoagulated rabbit blood is added dropwise to each of the samples (i.e., the centrifuge tubes which contains the composite materials and the Yunnan Baiyao), then 20 μL of 0.2 mol/L $CaCl_2$) solution are added into each the centrifuge tube, each the centrifuge tube is put into constant temperature shaker to be incubated for 15 min at a temperature of 37° C., 25 mL of deionized water is added into each the centrifuge tube, and each the centrifuge tube is shaked for 5 min at the constant temperature shake at a temperature of 37° C. A part of a solution in each the centrifuge tube is then taken out and an absorbance $A_{sample}$ of the part of the solution is measured with an ultraviolet spectrophotometer at a wavelength of 545 nm. 20 μL of fresh anticoagulated rabbit blood is added into a centrifuge tube as a blank group, then 25 mL of deionized water is added to dilute the fresh anticoagulated rabbit blood in the centrifuge tube, and an absorbance $A_{blank}$ of the centrifuge tube is measured at the same wavelength (i.e., 545 nm). A specific method for calculating BCI is as follows:

$$BCI = A_{sample}/A_{blank} \times 100\%$$

Figure 2:
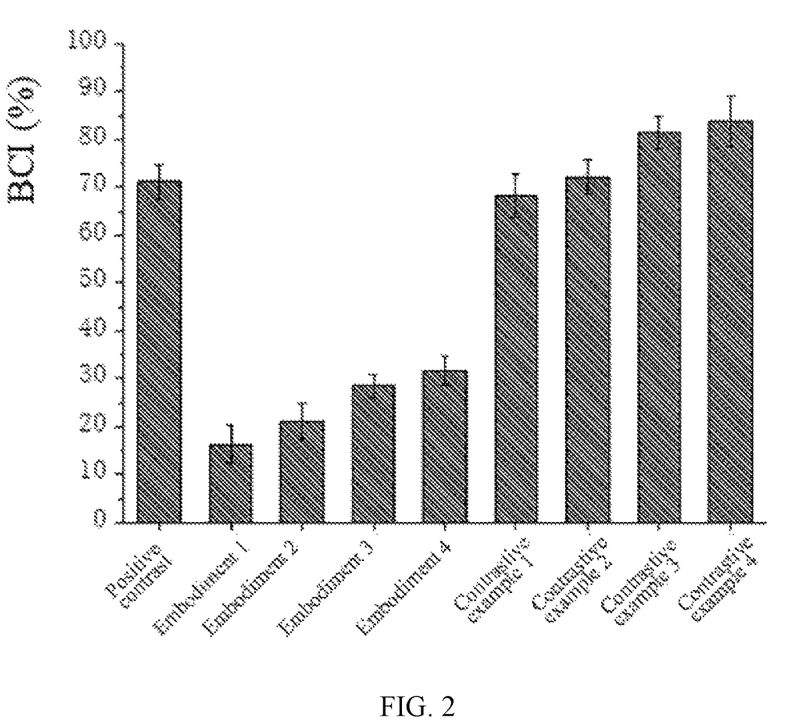
FIG. 2 illustrates a contrastive diagram of blood clotting indexes of the composite material for rapid blood clotting prepared by the disclosure.

Five parallel tests are performed on each of the test samples and the bland group. Test results of the five parallel tests are averaged to obtain an averaged result ($\bar{X}$) for each of the test samples and the blank group. Each the averaged result is analyzed by one-way analysis of variance (ANOVA) with SPSS19.0 (a software called Statistical Program for Social Sciences with a version of 19.0). $P<0.05$ and $p<0.01$ respectively indicate significant and high significant statistical differences in the averaged results, as shown in FIG. 2.

The smaller the BCI index, the better a blood clotting effect of a material. The clotting index results for the different test materials can be seen in FIG. 2. Yunnan Baiyao, also known as "Quhuanzhang Baibaodan", commonly known as "Baiyao", is a Chinese medicine for promoting blood circulation and removing blood stasis, which has a good effect on traumatic injury and traumatic hemorrhage, and is used as a positive contrast. BCI indexs of the composite material of the embodiments 1~4 are far lower than that of the positive contrast, with a very significant difference ($p<0.01$), showing a strong effect of promoting blood clotting. Especially the BCI index of the embodiment 1 is the lowest. Although the BCI indexs of the contrastive example 1 and contrastive example 2 are not significantly different from that of the positive contrast, the BCI indexs of the contrastive examples 1~4 are higher than those of the embodiments 1-4, indicating that effect of promoting blood clotting of the contrastive examples 1~4 is far lower than those of the embodiments 1~4.

Effective Test 2

Erythrocyte Adsorption Test:

Fresh anticoagulated whole blood is centrifuged at 2000 revolutions per minute (rpm) for 15 min, and erythrocytes at a lower layer are collected and diluted to a volume concentration of 10% with a phosphate buffer solution (PBS, pH=7.4), and thus an erythrocyte solution is obtained for later use. The composite materials prepared in the embodiments 1~4 and contrastive examples 1~4 are respectively cut into small pieces of 0.4 cm×0.4 cm with a scalpel, 500 μL of the erythrocyte solution is added to each of the small pieces, and each of the small pieces is incubated at a temperature of 37° C. for 1 h, and samples are taken out and washed twice in the PBS to remove unadhered erythrocytes from the samples. An erythrocyte solution without the composite material is used as a control group.

(1) Each of the samples are put into a 1% Triton-X100 solution at a temperature of 37° C. for 1 h to lyse adhered erythrocytes from the samples. An absorbance of each of the samples is measured at a wavelength of 540 nm, and the erythrocyte solution without the composite material is used as the control group.

Figure 4:
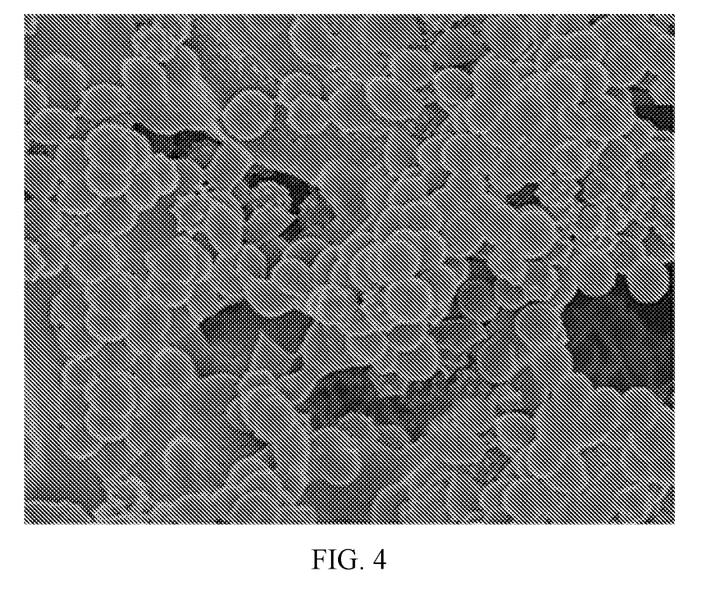
FIG. 4 illustrates a scanning electron micrograph of erythrocytes adsorbed by the composite material with rapid blood coagulation prepared in the embodiment 1 of the disclosure.

(2) The composite material of the embodiment 1 that has adsorbed erythrocytes is put in a glutaraldehyde solution with a concentration of 2.5% and fixed for 30 min, the composite material of the embodiment 1 is dehydrated with ethanol solutions with concentrations of 40%, 60%, 80%, and 100% for 15 minutes in turn, then the composite material of the embodiment 1 is naturally dried, and then a sample of the composite material of the embodiment 1 is obtained by ion-sputtering. The sample of the composite material of the embodiment 1 is observed by a scanning electron microscopy and recorded by photography, as shown in FIG. 4.

A Method for Calculating an Erythrocyte Adsorption Rate is as Follows:

Erythrocyte adsorption rate=$A_{sample}/A_{control} \times 100\%$

In this formula, $A_{sample}$ represents an absorbance of each of the samples, and $A_{control}$ represents an absorbance of the control group.

Figure 3:
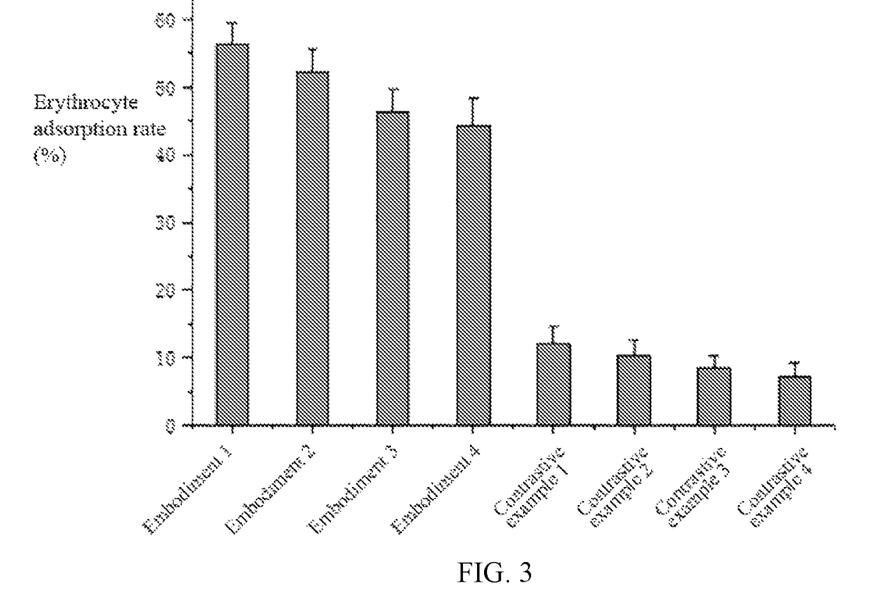
FIG. 3 illustrates a contrastive diagram of erythrocyte adsorption rates of the composite material for rapid blood clotting prepared by the disclosure.

The higher an adsorption rate of a material on erythrocytes, the better a blood clotting effect of a material. FIG. 3 illustrates the results of erythrocyte adsorption rates of different test materials. The erythrocyte adsorption rates of the composite materials of the embodiments 1~4 are higher than those of the composite materials of the contrastive examples 1~4, with a very significant difference ($p<0.01$), showing a strong effect of blood clotting, especially the effect of the embodiment 1 is the best. These results indicate that the composite material of embodiments 1~4 can use the chitosan-based Fe2+ complex to cross-coordinate with the hemoglobin of the erythrocytes to promote the adsorption and aggregation of the erythrocytes. In addition, the positive charge carried by the protonated amino group of chitosan attracts more erythrocytes with negative charge, which has a synergistic effect on the adsorption and aggregation of the erythrocytes, and promotes the rapid aggregation of a large number of erythrocytes to form blood clots.

From FIG. 4, it can be seen that the composite material of the embodiment 1 significantly promotes adsorption and aggregation of the erythrocytes, thereby to accelerate blood clotting.

Effective Test 3

Hemolysis Rate Test:

Hemolysis rate tests are performed on the composite materials of the embodiments 1~4 and the contrastive examples 1~4. The evaluation of the hemolysis rate tests refers to the "national standard GB/T14233 2-2005 Inspection Methods for Medical Infusion, Blood Transfusion, and Injection Equipment", and the hemolysis rate tests are performed as follows.

Fresh anticoagulant rabbit blood is taken and centrifuged at 2000 rpm at 4° C. for 15 min. The supernatant at an upper layer is removed and erythrocytes at a lower layer are collected, the erythrocytes are diluted to a volume concentration 2% with a phosphate buffer solution (PBS, pH=7.4) to obtain an erythrocyte solution for later use. 0.050 g of the composite material prepared in each of the embodiments 1~4 and contrastive examples 1~4 are added into a 1.5 mL centrifuge tube as test groups, then 500 μL of the PBS solution is added in to the centrifuge tube. After a constant temperature water bath is performed on the centrifuge tube at a temperature of 37° C. for 30 min, 500 μL of the erythrocyte solution is added into the centrifuge tube to mix with the composite material evenly, and another constant temperature water bath is performed on the centrifuge tube at a temperature of 37° C. for 1 h. 500 μL of distilled water is added into a centrifuge tube as a positive control group, and 500 μL of the PBS solution is added into a centrifuge tube as a negative control group. The parallel test is performed on each of the test groups, the positive control group, and the negative control group for 3 times. All the centrifuge tubes are respectively centrifuged at 2000 rpm at a temperature of 4° C. for 10 min, the supernatant of each of the centrifuge tubes is taken into an orifice plate, and an absorbance of each of the centrifuge tubes is measured at a wavelength of 540 nm with a microplate reader. The absorbance of the negative control group should not be greater than 0.03, and the absorbance range of the positive control group should be 0.80±0.20, otherwise the hemolysis rate tests should be restarted. The hemolysis rate is calculated as follows:

$$\text{Hemolysis rate (\%)} = \frac{A - A_0}{A_{100} - A_0} \times 100\%$$

In this formula, A represents an absorbance of each of the test groups, $A_0$ represents an absorbance of the negative control group, and $A_{100}$ represents an absorbance of the positive control group.

The hemolysis rate tests use an absorbance measurement method to measure an amount of hemoglobin released by erythrocytes after a material reacts with fresh anticoagulant blood, thereby to evaluate the safety of the material to the blood. When a hemolysis rate is tested according to the tests, if the hemolysis rate specified in the national standard is less than 5%, it is qualified.

Figure 5:
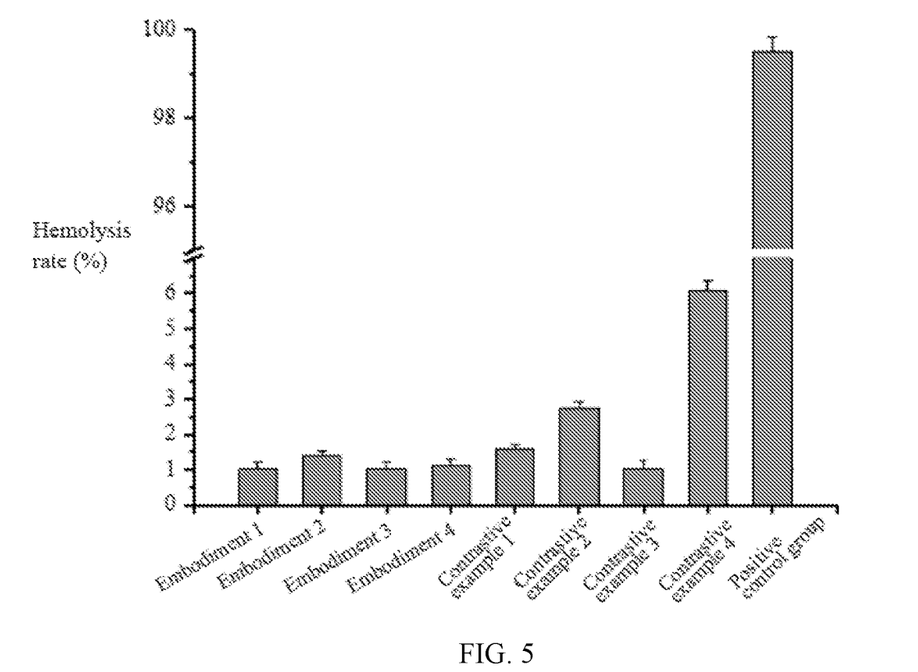
FIG. 5 illustrates a contrastive diagram of hemolysis rates of the composite material with rapid blood clotting prepared by the disclosure.

It can be seen from FIG. 5 that, except for the contrastive example 4, the hemolysis rates of the composite materials in the embodiments 1~4 and contrastive examples 1~3 are all less than 5%, which meet the qualification judgment index of biomaterials in the national standard GB/T 14233.2-2005 and meet the requirements of biomaterials on hemolysis, indicating that the prepared composite materials have good blood compatibility and high biological safety. In addition, the composite material prepared by the disclosure can rapidly absorb liquids and swell to form a hydrogel, and the composite material has a certain volume and is not easy to enter blood to cause thrombus.

The above embodiments only describe some embodiments of the disclosure, and do not limit the scope of the disclosure. On the premise of not deviating from the design spirit of the disclosure, various modifications and improvements made by those ordinary skilled in the art to the technical solutions of the disclosure should fall within the scope of protection defined in the claims of the disclosure.

What is claimed is:

1. A composite material for blood clotting, wherein the composite material is formed by using the following raw materials in parts by weight: 8 to 20 parts of chitosan, 7 to 14 parts of salicylaldehyde, 8 to 16 parts of 2-aminoisonicotinic acid, 1.5 to 3.5 parts of ferrous sulfate ($Fe^{2+}$ sulphate), 3 to 5 parts of a dopa compound, and 10 to 15 parts of disodium hydrogen phosphate;

wherein a chitosan-based $Fe^{2+}$ complex is formed by introducing the 2-aminoisonicotinic acid onto a molecular chain of the chitosan through an acylation reaction to obtain chitosan-amino isonicotinic acid graft, forming a Schiff base by condensation of the salicylaldehyde and amino groups of the 2-aminoisonicotinic acid, and combining the Schiff base with the ferrous sulfate;

wherein the composite material comprises: a charge transfer compound formed according to the dopa ingredient and the chitosan-based $Fe^{2+}$ complex;

wherein the composite material has a porous structure formed by interacting hydrogen phosphate anions of the disodium hydrogen phosphate with protonated amino groups of the chitosan to generate electrostatic and hydrogen bond effects;

wherein the composite material is in a form of solid; and the composite material forms a hydrogel after absorbing liquid;

a molecular mass of the chitosan is 50~300 kilodaltons (KDa), and a degree of deacetylation of the chitosan is 80~95%.

2. The composite material for blood clotting according to claim 1, wherein the raw materials are, in parts by weight, as follows: 14 parts of the chitosan, 10 parts of the salicylaldehyde, 12 parts of the 2-aminoisonicotinic acid, 2.5 parts of the ferrous sulfate, 4 parts of the dopa, and 13 parts of the disodium hydrogen phosphate.

3. The composite material for blood clotting according to claim 1, wherein the molecular mass of the chitosan is 100 KDa, and the degree of deacetylation of the chitosan is 90%.

4. The composite material for blood clotting according to claim 1, wherein the chitosan is 140 g, the salicylaldehyde is 100 g, the 2-aminoisonicotinic acid is 120 g, the ferrous sulfate is 25 g, the dopa is 40 g and the disodium hydrogen phosphate is 130 g.

* * * * *